United States Patent
Bui et al.

(10) Patent No.: US 9,320,700 B2
(45) Date of Patent: Apr. 26, 2016

(54) COSMETIC COMPOSITION INCLUDING ACID

(71) Applicant: L'OREAL, Paris (FR)

(72) Inventors: Hy Si Bui, Piscataway, NJ (US); Christopher Pang, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/218,263

(22) Filed: Mar. 18, 2014

(65) Prior Publication Data

US 2015/0265520 A1    Sep. 24, 2015

(51) Int. Cl.
| | |
|---|---|
| *A61K 8/81* | (2006.01) |
| *A61K 8/19* | (2006.01) |
| *A61K 8/362* | (2006.01) |
| *A61Q 1/10* | (2006.01) |
| *A61K 8/365* | (2006.01) |

(52) U.S. Cl.
CPC ............... *A61K 8/8147* (2013.01); *A61K 8/19* (2013.01); *A61K 8/362* (2013.01); *A61K 8/365* (2013.01); *A61K 8/8117* (2013.01); *A61Q 1/10* (2013.01); *A61K 2800/30* (2013.01); *A61K 2800/33* (2013.01); *A61K 2800/43* (2013.01); *A61K 2800/48* (2013.01)

(58) Field of Classification Search
CPC ....... A61K 8/8147; A61K 8/362; A61K 8/19; A61K 2800/30; A61K 2800/43; A61K 8/365; A61Q 1/10
USPC .......................................................... 424/401
See application file for complete search history.

(56) References Cited

U.S. PATENT DOCUMENTS

| | | | |
|---|---|---|---|
| 4,104,262 A | 8/1978 | Schade | |
| 6,333,039 B1 * | 12/2001 | Fendler et al. | ................ 424/401 |
| 6,517,823 B1 | 2/2003 | Norman et al. | |
| 2006/0234886 A1 * | 10/2006 | Massaro et al. | ............... 510/130 |
| 2010/0028284 A1 | 2/2010 | Atis et al. | |
| 2011/0195035 A1 * | 8/2011 | Vondruska et al. | ............. 424/59 |
| 2013/0084255 A1 | 4/2013 | Li et al. | |
| 2013/0084256 A1 | 4/2013 | Li et al. | |
| 2013/0236406 A1 | 9/2013 | Tong et al. | |

(Continued)

FOREIGN PATENT DOCUMENTS

| | | |
|---|---|---|
| EP | 1367080 A1 | 12/2003 |
| WO | 2008155059 A2 | 12/2008 |
| WO | 2013092380 A1 | 6/2013 |

OTHER PUBLICATIONS

N. Reddy, Y. Yang, Citric acid cross-linking of starch films (2009), Faculty Publications—Textiles, Merchandising and Fashion Design, Paper 25, http://digitalcommons.unl.edu/textiles_facpub/25; Food Chemistry 118:3 (Feb. 1, 2010) 702-711, doi: 10.1016/j.foodchem. 2009.05.050, 2009 Elsevier Ltd.

(Continued)

*Primary Examiner* — Blessing M Fubara
(74) *Attorney, Agent, or Firm* — Oblon, McClelland, Maier & Neustadt, L.L.P.

(57) ABSTRACT

The present invention relates to a cosmetic composition comprising a latex film forming polymer, an acid, water and optionally a pigment, said composition having a pH of from about 6.5 to about 8. The invention also relates to a method for making up and/or enhancing the appearance of a keratinous substrate, in particular lashes, by applying these compositions to the keratinous substrate.

13 Claims, 3 Drawing Sheets

Viscosity of mascaras with different concentrations of citric acid at various shear rate.

(56) References Cited

U.S. PATENT DOCUMENTS

| | | |
|---|---|---|
| 2013/0236407 A1 | 9/2013 | Tong et al. |
| 2013/0236408 A1 | 9/2013 | Bui et al. |
| 2013/0236409 A1 | 9/2013 | Bui et al. |
| 2015/0079016 A1* | 3/2015 | Bolognini et al. ........... 424/70.7 |

OTHER PUBLICATIONS

J.L. Keddie, Film formation of latex, Materials Science and Engineering, 21 101-170, Reports: A Review Journal, 1997 Elsevier Science S.A.

J.Y. Charmeau, E. Kientz, Y. Holl, Adhesion of latex films; influence of surfactants, Progress in Organic Coatings 27 (1996) 87-93, Elsevier Science S.A.

J.Y. Charmeau, R. Berthet, C. Gringreau and Y. Holl, E. Kientz, Effects of film structure on mechanical and adhesion properties of latex films, Int. J. Adhesion and Adhesives 7 (1997) 169-176 vol. 12, Elsevier Science Limited, printed in Great Britain.

D.I. Lee, The effects of latex coalescence and interfacial crosslinking on the mechanical properties of latex films, Polymer 46 (2005) 1287-1293, Science Direct, www.elsevier.com/locate/polymer.

A. Olah, M.A. Hempenius, S. Zou, G.J. Vancso, Adhesion studies of latex film surfaces on the meso- and nanoscale, Applied Surface Science 252 (2006) 3714-3728, www.elsevier.com/locate/apsusc.

S. Kiil, Drying of latex films and coatings: Reconsidering the fundamental mechanisms, Progress in Organic Coatings 57 (2006) 236-250, www.elsevier/locate/progcoat.

P.A. Steward, J. Hearn, M.C. Wilkinson, An overview of polymer latex film formation and properties, Advances in Colloid and Interface Science 86 (2000) 195-267; www.elsevier.nl/locate/cis.

U.S. Appl. No. 14/218,229, filed Mar. 18, 2014, Bui et al.

* cited by examiner

Viscosity of core compositions at different shear rate versus concentration of citric acid Viscosity of mascaras with different concentrations of citric acid at various shear rate.

Heat flow vs. Temperature of core compositions at different citric acid concentrations Heat flow vs. Temperature of mascaras at different citric acid concentrations

COSMETIC COMPOSITION INCLUDING ACID

TECHNICAL FIELD

The present invention relates to a cosmetic wax-free, water based composition and method for making up and/or enhancing the appearance of a keratinous substrate, the composition comprising at least one latex film forming polymer, at least one acid, and water. The compositions of the present invention optionally may contain at least one colorant.

BACKGROUND OF THE INVENTION

Makeup products, especially mascaras, are expected to have good wear and transfer resistance properties. With regard to this expectation, currently marketed mascaras are typically comprised of an emulsion of water and waxes to provide volume, length, and other attributes. Mascaras often also include one or more polymers to improve these properties. Illustrations of these polymers include silicone resins, polyacrylates and lattices. See, U.S. Pat. No. 6,517,823 and US2010/0028284. However, the above-mentioned polymers, which are advantageous in terms of wear and transfer-resistance properties, are often found by consumers to be difficult to spread and provide an undesirable tacky feeling. Moreover, the current long wear mascaras typically need to be reapplied approximately every 12-16 hour period. There remains a need to provide make up, particularly mascara, which affords longer wear (no flaking, stable color, does not transfer), for five (5) days or more (extremely long wear) and is still stable and comfortable to the consumer.

It has been found that the combination of a latex film forming polymer, a polycarboxylic acid and water, in the stated amounts, provides a very stable and comfortable long wear cosmetic composition even in the absence of fats and waxes. This composition unexpectedly enables the manufacture of extreme wear mascara lasting up to 5 days after application without flaking and with improved adhesion to the lashes ("extreme long wear"). Moreover, because the compositions are water-based they are ecologically preferred to oil-based compositions.

The use of citric acid to cross-linking a starch film has previously been discussed. See N. Reddy et al., "Citric acid cross-linking of starch films" (2009) Faculty Publications—Textiles, Merchandising and Fashion Design (DigitalCommons@University of Nebraska-Lincoln) at p. 25. The use of esters of tricarboxylic acids, including citric acid, as film plasticizers is discussed in WO2013/092380 (L'Oreal). Applicants have unexpectedly found that the use of a polycarboxylic acid with a latex film forming polymer not only enhances the viscosity of the composition and assists in the suspension of pigments in the composition, but also increases the adhesion of the film forming polymer to keratinous fibres, particularly lashes, resulting in a mascara having extremely long wear.

BRIEF SUMMARY OF THE INVENTION

The present invention relates to homogeneous cosmetic compositions for making up and/or enhancing the appearance of keratinous substrates comprising:
(a) at least one latex film forming polymer;
(b) at least one acid;
(c) water; and
(d) optionally, at least one pigment;

wherein said composition has a viscosity from about 0.01 Pa·s to about 1500 Pa·s at a shear rate of 1/s and a pH of from about 6.5 to about 8.

The foregoing composition may include additional components compatible with the composition and typically used in cosmetics, in particular mascaras. These compositions are preferably devoid of waxes and emulsifiers.

Another aspect of the present invention is a method of making up and/or enhancing the appearance of a keratinous substrate, in particular eye lashes, comprising applying onto the keratinous substrate the above-disclosed composition, wherein the composition provides a creamy, flexible film texture, great comfort and transfer resistance properties for up to 5 days of wear.

DESCRIPTION OF THE INVENTION

Figure 1:
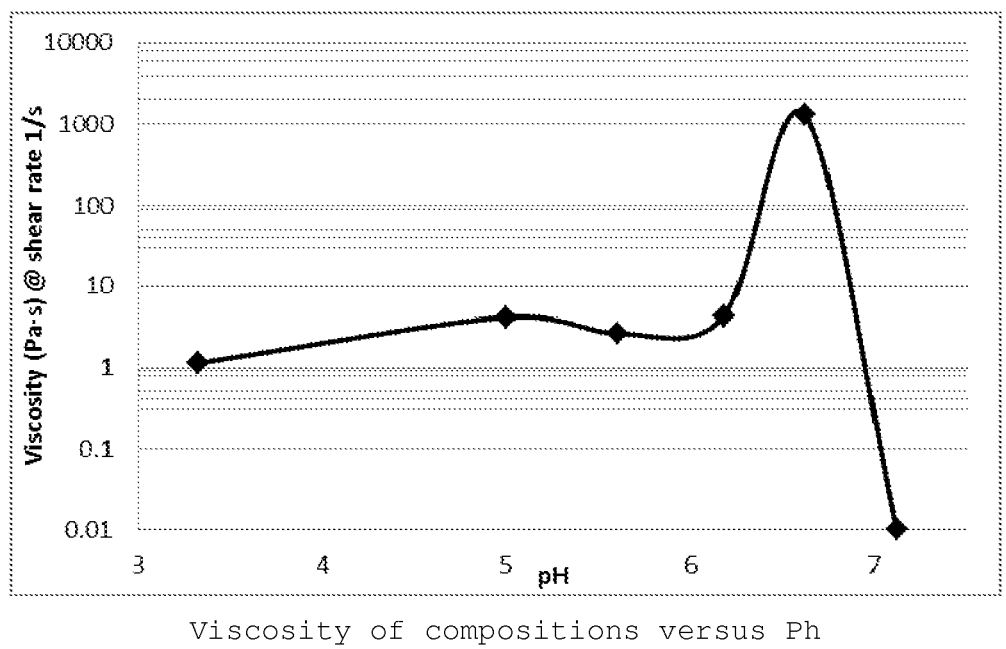
FIG. 1 is rheological data (using an ARG 2 Rheometer) showing the effect of pH on viscosity of exemplified compositions at a shear rate of 1/s.

Other than in the operating examples, or where otherwise indicated, all numbers expressing quantities of ingredients and/or reaction conditions are to be understood as being modified in all instances by the term "about."

"About" as used herein means within 10% of the indicated number (e.g. "about 10%" means 9%-11% and "about 2%" means 1.8%-2.2%).

"At least one" means one or more and thus includes individual components as well as mixture/combinations.

The term "glass transition temperature" (Tg) generally refers to the temperature at which amorphous material changes from a glassy solid state to a rubbery state. The temperature may be measured by standard techniques in the art, such a Differential Scanning Calorimetry (DSM), e.g., according to a standard protocol such as ASTM D3418-97 standard.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of waxes" means that waxes are preferably omitted (that is 0% by weight), but can be present in the composition at an amount of less than about 0.25% by weight, typically less than about 0.1% by weight, typically less than about 0.05% by weight, based on the total weight of the composition as a whole.

"Keratinous substrate" may be chosen from, for example, hair, eyelashes, lip, and eyebrows, especially eye lashes.

"Low Tg" or "Low Glass Transition Temperature" as used herein to describe the films made with the compositions of the invention means that the films have a glass transition temperature (Tg) of from about 0° C. to about 20° C.

"Polymers" as defined herein, include homopolymers and copolymers formed from at least two different types of monomers.

"Percent strain" (or sometimes referred to as percent elongation) as used herein is the amount of deformation (here elongation or stretch) that a film according to the invention experiences when stressed (e.g. pulled) compared to its original shape/size. For example, if a 10 cm film is deformed so that it becomes 11 cm long, the strain is (11-10)/10=0.1, which can also be expressed in percent measurement, in this example 10%.

"Water-dispersible" with respect to the film forming polymer herein means that the polymer is dispersible in water at 25° C. in an amount of at least 70% in the presence of a surfactant.

The "wear" of compositions as used herein, refers to the extent by which the composition remains creamy and flexible when applied, for example to lashes, does not substantially flake and retains the same or substantially the same color as at the time of application, as viewed by the naked eye, after a certain period or an extended period of time. Wear properties may be evaluated by any method known in the art for evaluating such properties. For example, wear may be evaluated by a test involving the application of a composition to eye lashes and evaluating the color of the composition after a specified period of time. Further, these characteristics may be evaluated with respect to other compositions, such as commercially available compositions. "Extreme wear" with respect to mascara refers to mascara having good wear properties for up to at least 5 days after application.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

In an embodiment, the invention relates to a cosmetic composition comprising
(a) at least one latex film forming polymer;
(b) at least one acid;
(c) water; and
(d) optionally, at least one pigment;
wherein said composition has a viscosity from about 0.01 Pa·s to about 1500 Pa·s at a shear rate of 1/s and a pH of from about 6.5 to about 8.

In another embodiment the invention relates to a cosmetic composition comprising
(a) at least one latex film forming polymer;
(b) at least one acid; and
(c) water;
wherein said composition has a viscosity from about 0.01 Pa·s to about 1500 Pa·s at a shear rate of 1/s and a pH of from about 6.5 to about 8.

In another embodiment the invention relates to a cosmetic composition comprising
(a) at least one latex film forming polymer having a glass transition temperature from about −15° C. to about 90° C.;
(b) at least one acid;
(c) water; and
(d) at least one pigment;
wherein said composition has a viscosity from about 70 Pa·s to about 350 Pa·s at a shear rate of 1/s and a pH of from about 6.5 to about 8.

Another embodiment of the invention relates to a cosmetic composition comprising
(a) from about 20% to about 40%, by weight, of at least one latex film forming polymer selected from acrylate copolymers and derivatives thereof having a glass transition temperature from about −15° C. to about 90° C.;
(b) from about 0.5% to about 0.9%, by weight, of at least one acid;
(c) from about 40% to about 80% by weight, water; and
(d) optionally, at least one pigment;
wherein said composition has a viscosity from about 0.01 Pa's to about 1500 Pa·s, at a shear rate of 1/s, and a pH of from about 6.5 to about 8, and wherein all weights are relative to the total weight of the composition.

Another embodiment of the invention relates to a cosmetic composition comprising
(a) from about 20% to about 40%, by weight, of at least one latex film forming polymer selected from acrylate copolymers and derivatives thereof having a glass transition temperature from about −15° C. to about 90° C.;
(b) from about 0.5% to about 0.9%, by weight, of at least one acid;
(c) from about 40% to about 60% by weight, water; and
(d) at least one pigment;
wherein said composition has a viscosity from about 70 Pa's to about 350 Pa·s, at a shear rate of 1/s, and a pH of from about 6.5 to about 8, and wherein all weights are relative to the total weight of the composition.

Without being bound by theory, it is believed the acid forms a complex with the latex polymer through interactions between the polar groups of the acid with those of the anionic styrene acrylate copolymer. The resulting network is more structured and firm resulting in a thicker composition with enhanced adhesive properties (longer wear). It is also postulated that in the current invention the acid is not acting as a plasticizer. While typical plasticizers significantly lower the Tg of the resulting films making the films softer and more flexible, the acid in the current invention lowers the Tg of the resulting film only slightly resulting in a stronger and more robust film while also allowing for suspension of the pigment, yet not making the film so brittle that it breaks and flakes upon use in a cosmetic composition.

The compositions of the invention result in films having a glass transition temperature (Tg) of from about 14° C. to about 30° C., preferably from about 18° C. to about 28° C.

In a particular embodiment, the core compositions of the invention devoid of pigments result in films having a Tg of from about 25° C. to about 28° C.

In another particular embodiment, mascaras made with the core compositions of the invention and including pigments result in a film having a Tg of from about 14° C. to about 22° C., optimally from about 18° C. to about 21° C., as measured by differential scanning calorimetry (DSC).

In an embodiment, the viscosity of mascaras made with the inventive compositions, measured with an AR G2 Rheometer, is greater than or equal to 70 Pa·s, typically from about 70 Pa·s to about 350 Pa·s at 1/s shear rate, more typically from about 75 Pa·s to about 300 Pa·s at 1/s shear rate, including all ranges and subranges therebetween. The viscosity is generally measured over a 10 minute duration.

In another embodiment, the pH of the compositions of the invention at 25° C. ranges from about 6.5 to about 8, most preferably about 7.0+/−0.5.

Typically, the compositions of the invention are dispersions. These compositions are particularly useful in the preparation of water-based, water-proof mascaras.

Latex Film Forming Polymer (a)

The at least one latex film forming polymer may be chosen from random styrene acrylate copolymers and derivatives thereof. Such copolymers are described, for example, in US 2013/0084256 and US 2010/0028284, both of which are herein incorporated by reference. In an embodiment the at least one styrene acrylate copolymer and derivatives thereof may be chosen from those copolymers that are water-dispersible and have a glass transition temperature (Tg) ranging from about −15° C. to about 90° C., such as from about 0° C. to about 50° C. The term "water-dispersible" with respect to polymers is well-understood by one skilled in the art. See, e.g. U.S. Pat. No. 4,104,262. By way of non-limiting example, the at least one film-forming styrene acrylate copolymer may be chosen from styrene/acrylates/ammonium methacrylate copolymers, styrene/acrylates copolymers emulsion (INCI name), styrene acrylic copolymers, and mixtures thereof. Exemplary commercial random styrene acrylate copolymer products that may be used in the invention include, but are not limited to, SYNTRAN™, 5760 (styrene/acrylates/ammonium methacrylate copolymer (and) butylene glycol (and) sodium laureth-12 sulphate (INCI name), commercially available from Interpolymer Corporation); JONCRYL™ 77 (styrene/acrylates copolymer in the form of an ammonia salt, along with water and polypropylene glycol, available from BASF Performance Chemicals); and RHOPLEX™ P376 (styrene/acrylates copolymer available from Dow Chemical Company).

In a particular embodiment the film forming the latex film former is styrene/acrylate copolymer.

In an embodiment the at least one film forming styrene acrylate copolymer may be present in the cosmetic composition in an amount ranging from about 20% to about 40%.

In another embodiment where mascaras are made with the inventive core compositions, the at least one film forming styrene acrylate copolymer may be present in the mascara compositions in an amount ranging from about 20% to about 37.5% by weight, such as from about 30% to about 36.5% by weight, most particularly from about 34% to about 36% by weight, including all ranges and subranges therebetween, relative to the total weight of the composition.

Acid (b)

Acids useful in the invention are those that will result in a composition having a pH of from about 6.5 to about 8 when added in amounts not typically exceeding about 0.9% by weight relative to the final composition. The acids preferably are cosmetically compatible with and acceptable for use on hair, eyes, lashes and skin at the given Normality.

In an embodiment, the acid is "strong acid." As used herein a "strong acid" is an acid having a pH of from about 1.0 to about 2.4 at Normality of 0.1 N. Non-limiting examples of such acids include citric, isocitric, formic, hydrochloric, lactic, malic, oxalic, tartaric and trichloacetic acids, and mixtures thereof.

Another useful acid is saturated salicylic acid.

According to a preferred embodiment, the acid is selected from malic, citric and isocitric acids, and mixtures thereof. In a particularly preferred embodiment the acid is citric acid.

When the acid has pH of from about 1.0 to about 2.4 at Normality of 0.1 N, it may be present in the cosmetic composition in an amount ranging from about 0.5% to about 0.9% by weight, such as from about 0.6% to about 0.89% by weight, most particularly from about 0.8% to about 0.85% by weight, including all ranges and subranges therebetween, relative to the total weight of the composition. Applicants have surprising found that 0.5% to 0.9% is a critical range for a "strong acid" in the inventive compositions. Below a strong acid amount of 0.5% the composition tends to be too fluid to provide optimal application (for example too runny to apply to lashes) and at amounts of strong acid above 0.9% the resulting film upon drying (e.g. on the lashes) is crusty and tends to flake off.

Water (c)

The compositions for the invention also comprise water in an amount ranging from about 40% to about 80% by weight, preferably from about 45% to about 75% by weight, most typically from about 50% about 60% by weight, in particular about 52% by weight, including all ranges and subranges therebetween, relative to the total weight of the compositions.

Pigment(s)(d)

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention, including but not limited to, surface treatments with compounds such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. In an embodiment of the invention the pigment is present in an amount of from about 10% to about 15% by weight, more particularly 12% by weigh based on the total weight of the composition.

Additional Optional Additive(s)

A composition according to the invention may also comprise at least one agent usually used in cosmetics, chosen, for example, from: reducing agents; thickeners; film-forming agents that are especially hydrophobic, or are softeners, antifoams, moisturizers, or UV-screening agents; ceramides; cosmetic active agents; peptizers; fragrances; proteins; vitamins; propellants; hydrophilic or lipophilic, film-forming or non-film-forming polymers; lipophilic or hydrophilic gelling agents; liquid lipids; shine agents; fibers, such as nylon fibers; and preservatives, such as for example phenoxyethanol and caprylyl glycol. A non-exhaustive listing of such ingredients is found in U.S. Pat. No. 7,879,316, the entire content of which is hereby incorporated by reference. Additional examples of additives may be found in the *International Cosmetic Ingredient Dictionary and Handbook* ($9^{th}$ ed. 2002, and subsequent editions).

In an embodiment, the composition includes at least one preservative selected from phenoxyethanol, caprylyl glycol, and a mixture thereof.

The shine agents may be chosen from silicones (oils and elastomers), alkoxylated silicone, oils, ethoxylated oils, fats, esters, transesters, hydrocarbons, quats and mixtures thereof. Non-limiting examples of shine agents include amodimethicone, dimethicone, dimethiconol, cyclemethicone, phenyltrimethicone, aminopropyl phenyltrimethicone, trimethyl pentaphenyl trisiloxane, cetyl dimethicone, alkyl dimethicone, potassium dimethicone PEG-7 pantheyl phosphate, olive oil, jojoba oil, apricot oil, avocado oil, castor oil, lanolin, squalane, capric/caprylic triglyceride, octyl palmitate, isopropyl palmitate, isopropyl myristate, mineral oil, petrolatum, polyquaternium-4, polyquaternium-11, behentrimonium methosulfate, benetrimonium chloride and mixtures thereof.

While the compositions of the invention may include additional components as listed above, it is significant that these compositions possess desirable cosmetic properties, for example extended wear in mascaras, and have good product integrity such as volume and thickness, even without containing thickeners, waxes or emulsifiers.

Cosmetic Methods

In an embodiment according to the invention, the compositions comprising a film forming latex polymer, an acid, and water can impart thickening and volumizing properties to the lashes and remain on the lashes in substantially the same form and amount for at least 5 days. Accordingly, another embodiment of the invention provides a method of making up/or enhancing the appearance of eyelashes by applying to the lashes topically the composition of the present invention in a sufficient amount to make up the lashes. The compositions may be applied to the eyelashes as needed, but preferably the composition does not need to be reapplied for about 5 days.

Another embodiment of the invention relates to a method of improving long wear and adhesion of a mascara while retaining comfort, buildability, color intensity properties of said mascara by incorporating therein at least one forming latex polymer, one acid and water as described herein.

EXAMPLES

The following Examples are intended to be non-restrictive and explanatory only, with the scope of the invention being defined by the claims.

As used in herein INCI US stands for International Nomenclature of Cosmetic Ingredients US.

In Table 1 below, compositions without pigments and including different concentrations of citric acid were prepared and their physical properties (Tg, viscosity, pH, and particle sizes) were measured. A composition containing hylauraonic acid (not a "strong acid") was prepared as a comparator.

TABLE 1

Impact of Acid and Amounts Thereof on Film Forming Latex Polymer

| INCI US Name (and component function in formula) | Ex 1 (wt %) (comparator) | Ex 2 (wt %) (comparator) | Ex 3 (wt %) (comparator) | Ex 4 (wt %) (comparator) | Ex 5 (wt %) (inventive) | Ex 6 (wt %) (inventive) | Ex 7 wt %) (comparator) |
|---|---|---|---|---|---|---|---|
| styrene/acrylates copolymer (Joncryl ™ 77) (a) | 20 | 20 | 20 | 20 | 20 | 20 | 20 |
| citric acid (b) | 3.0 | 1.4 | 1.2 | 1.0 | 0.7 | 0.6 | 0 |
| hyaluraonic acid (comparative) | 0 | 0 | 0 | 0 | 0 | 0 | 2.43 |
| water (c) | 77 | 78.6 | 78.8 | 79 | 79.3 | 79.4 | 77.57 |
| viscosity (Pa·s) @ shear rate 1/s | 1.14 | 4.17 | 2.65 | 4.3 | 1303 | 0.01 | 0.47 |
| pH | 3.32 | 5.0 | 5.6 | 6.18 | 6.62 | 7.12 | 8.13 |
| particle Size (um) | 59 | 14 | 108 | 22 | 0.03 | 0.06 | 0 |
| Tg (° C.) | 28.51 | 27.78 | 26.63 | 24.37 | 27.42 | 25.29 | 0 |

If present, the above additives are typically found in an amount for each of them of between about 0.01% and about 10% by weight, most typically from about 0.5% to about 2% by weight, including all ranges and subranges therebetween, by weight relative to the total weight of the composition. A person skilled in the art will take care to select the constituents of the composition such that the advantageous properties associated with the invention are not, or are not substantially, adversely affected.

All numerical values in the above Table 1 are weight percent active. The pH of the hyaluronic acid at 0.1N was about 4.68.

As is shown in Table 1 and in FIG. 1, the optimal pH of the compositions is from about 6.5 to about 7.5, more preferably from about 6.6 to about 7.2, most preferably from about 6.8 to about 7.1. In this range the compositions exhibit increased viscosity. Maximum viscosity increase is at about pH 6.8.

As the pH is increased beyond about 7.2, the viscosity of the composition decreases as shown in Table 1 and FIG. 1.

Figure 4:
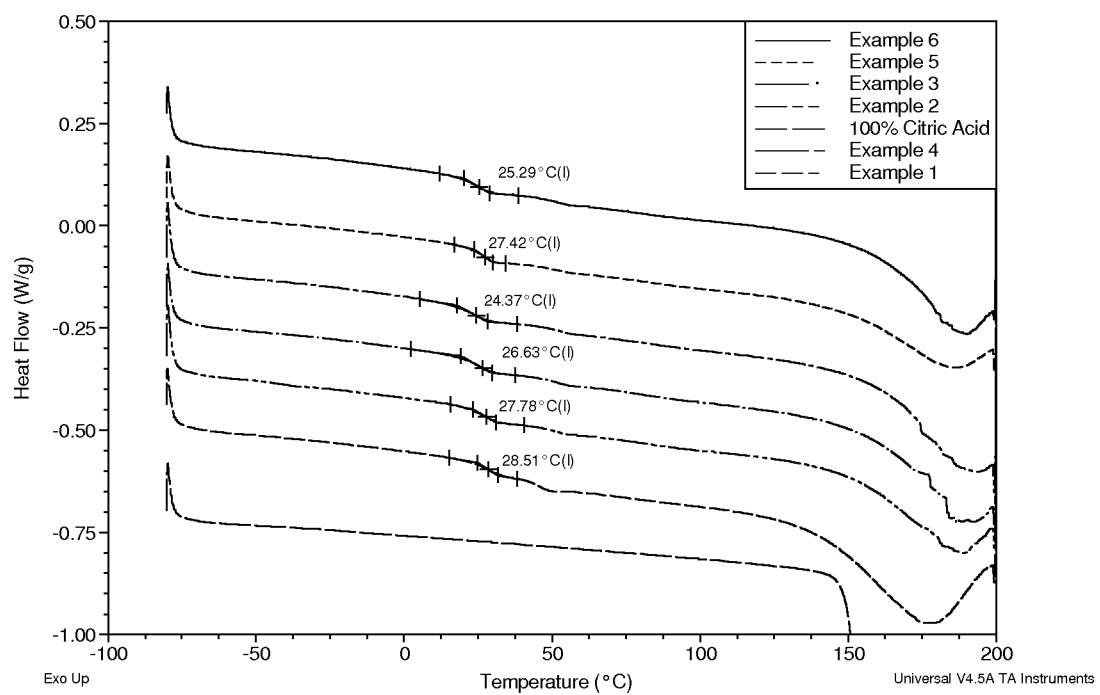
FIG. 4 is a differential scanning calorimetric (DSC) scan showing heat flow at different temperatures of core compositions (no pigments) having different amounts of citric acid. This figure provides the glass transition temperature (Tg) of the exemplified compositions.
Figure 5:
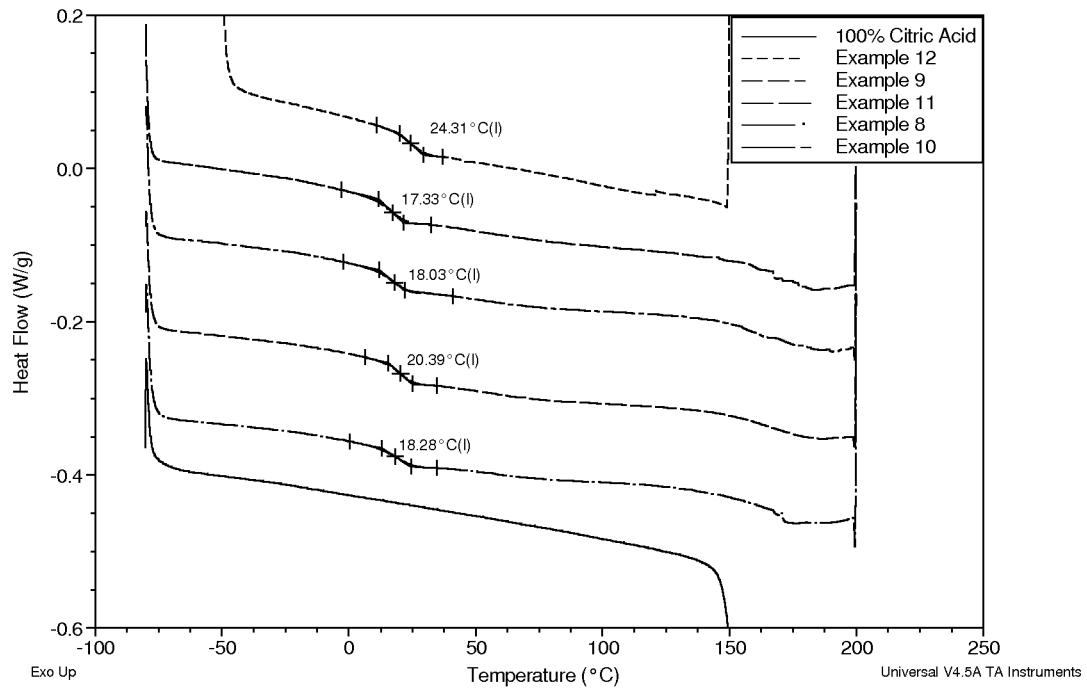
FIG. 5 is a differential scanning calorimetric (DSC) scan showing heat flow at different temperatures of mascara compositions (with pigments) having different amounts of citric acid.

Table 1 and FIG. 4 show that at different citric acid concentrations, the Tg of the films resulting from the inventive compositions did not change drastically. This indicated the citric acid did not act as a conventional plasticizer with respect to the styrene/acrylates copolymer film former.

Figure 2:
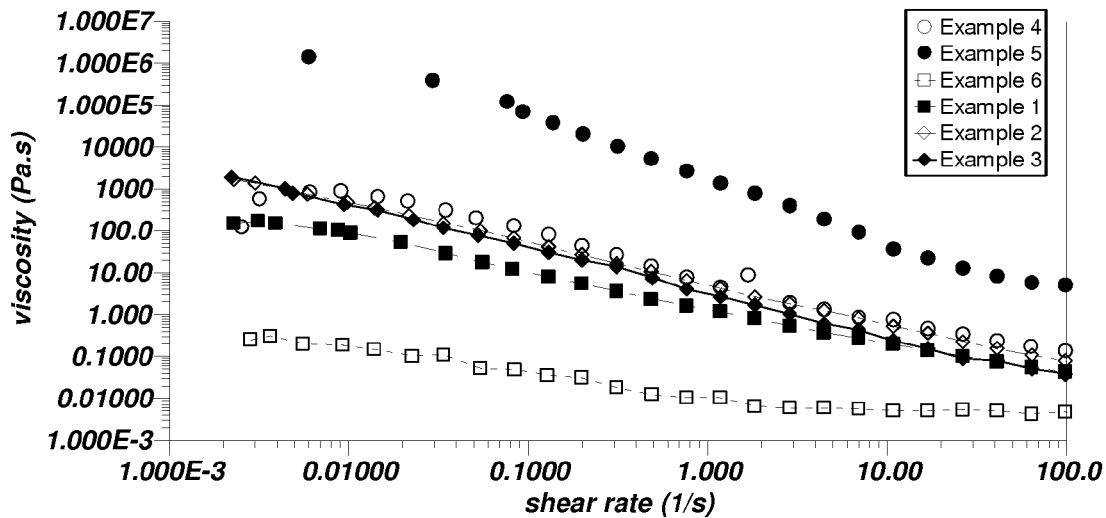
FIG. 2 is rheological data (using an ARG 2 Rheometer) showing the viscosity at varying shear rates of core compositions (no pigments) having different citric acid concentrations.

FIG. 2 shows the viscosity at varying shear rates of core compositions (no pigments) having different citric acid concentrations.

Figure 3:
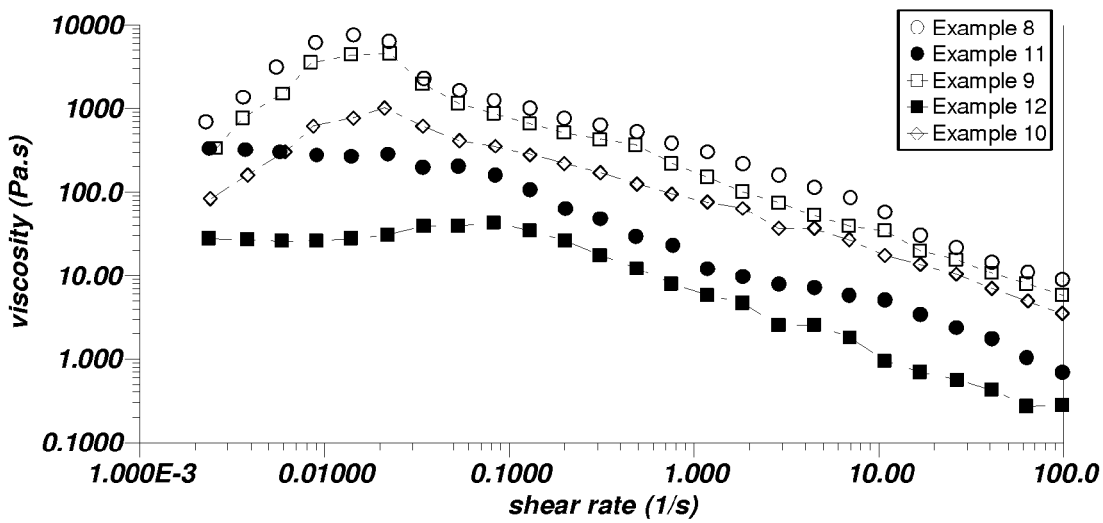
FIG. 3 is rheological data (using an ARG 2 Rheometer) showing the viscosity at varying shear rates of exemplified mascara compositions (include pigments) having different citric acid concentrations.

Similarly, FIG. 3 shows the viscosity at varying shear rates of exemplified mascara compositions (include pigments) having different citric acid concentrations.

Method of Preparation of Mascaras

Citric acid was first dissolved in water and slowly introduced dropwise into the latex polymer while mixing with propeller blade over a course of 10 min. Mixing continued with propeller at 300-2000 rpm until homogeneous. All the materials were then combined into plastic cup container and placed in a speed mixer DAC 400 and mixed at 2750 rpm for 5 mins or until homogeneous. The mixture was then cooled (deaerated) to room temperature while mixing with a propeller blade before transferring to suitable size containers for testing.

Sample mascaras prepared as describe above are exemplified in Table 2 below.

In-Vivo Testing: Consumer Flash

The flake, smudge and overall wear properties of mascaras made with the inventive core compositions (Examples 8, 9, and 10) and a comparator mascara (Example 12) were evaluated on test subjects. Each mascara was evaluated on 3-5 test subjects.

Protocol for Consumer Flash:

Mascara was applied by the test subjects and worn for five (5) days without reapplication. The subjects otherwise maintained their normal routines, such as showering, etc. The results of this evaluation are reported in Table 2 above.

As is shown in Table 2 above, the compositions of the invention (Ex. 8, 9, and 10) had longer wear than and comparable transfer resistance to the comparator (Ex. 12). Moreover, the inventive mascaras had these desirable properties even without further additives such as thickeners. Thus, in one embodiment, the compositions of the invention are free of thickeners.

The results of the in vivo testing show that the presence of the citric acid in the inventive compositions improves the adhesion of the mascara onto the lashes. After 5 days, the mascara was still on the lashes.

TABLE 2

Mascara Compositions

| INCI US Name (and component function in formula) | Ex 8 (wt %)[1] (inventive) | Ex 9 (wt %) (inventive) | Ex 10 (wt %) (inventive) | Ex 11 (wt %) (Comparator) | Ex 12 (wt %) (Comparator) | Ex 13 (wt %) (Comparator) |
|---|---|---|---|---|---|---|
| styrene/acrylates copolymer (Joncryl ™ 77) (a) | 34.44 | 34.44 | 34.44 | 34.44 | 34.44 | 34.44 |
| citric acid (b) | 0.9 | 0.85 | 0.72 | 0.48 | 0 | 1.2 |
| water (c) | 51.06 | 51.61 | 51.74 | 51.98 | 52.46 | 51.26 |
| caprylyl glycol (preservative) | 0.4 | 0.4 | 0.4 | 0.4 | 0.4 | 0.4 |
| phenoxyethanol (preservative) | 0.7 | 0.7 | 0.7 | 0.7 | 0.7 | 0.7 |
| iron oxides (pigment) | 12 | 12 | 12 | 12 | 12 | 12 |
| Expert Gel (thickener) | 0.5 | | | | | |
| viscosity (Pa · s) @ Shear rate 1/s | 296.3 | 150 | 75.03 | 11.68 | 5.8 | Powder |
| pH | 7.10 | 6.97 | 7.06 | 7.29 | 8.05 | 6.47 |
| in vitro sebum 24 hr | No transfer | No transfer | No transfer | No transfer | No transfer | No transfer |
| in vitro water 24 hr | No transfer | No transfer | No transfer | No transfer | No transfer | No transfer |
| Tg (° C.) | 18.5 | 20.39 | 18.03 | 17.33 | 24.31 | n/a |
| in vivo test (# days)[2] | 3.6 | 5 | 4 | n/A | 2 | n/A |

[1]All numerical values in the above Table 2 are weight percent active.
[2]Number of days consumers (3-5 persons per mascara) perceived compositions to have good wear.

Evaluation Procedures

Assessment of Incorporation of Citric Acid on Tg of Resulting Film:

The inventive compositions as well as mascara formulas incorporating the inventive compositions were drawn down on a glass plate using a draw dawn bar until the thickness of the resulting film was about 6 mil. The films were allowed to dry from overnight to a week. The dried films were then peeled from the plate and each was then subjected to DSC scanning to measure film softening. The results of this test are reported in Table 1 above with respect to inventive core compositions comprising citric acid+styrene acrylates/copolymer+water and in Table 2 with respect to mascara formulas incorporating said compositions.

It is to be understood that the foregoing describes preferred embodiments of the invention and that modifications may be made therein without departing from the spirit or scope of the invention as set forth in the claims.

The invention claimed is:

1. A cosmetic composition comprising:

(a) about 20% to about 40% by weight, based on the total weight of the cosmetic composition, of at least one latex film forming polymer;

(b) at least one acid;
(c) water; and
(d) optionally, at least one pigment;
wherein said composition has a viscosity from about 0.01 Pa·s to about 1500 Pa·s at a shear rate of 1/s and a pH of from about 6.5 to about 8,
wherein the latex film forming polymer is an acrylate copolymer having a glass transition temperature from about −15° C. to about 90° C.,
wherein the acrylate copolymer is selected from the group consisting of styrene/acrylates/ammonium methacrylate copolymers, styrene/acrylates copolymers emulsion, styrene acrylic copolymers, and mixtures thereof, and
wherein the acid is selected from the group consisting of citric acid, isocitric acid, formic acid, hydrochloric acid, lactic acid, malic acid, oxalic acid, tartaric acid, trichloroacetic acid, and mixtures thereof.

2. The compositions of claim 1 wherein the acid has a pH of from about 1.0 to about 2.4 at Normality of 0.1 N.

3. The composition of claim 2 wherein the acid is present in an amount of from about 0.5% to about 0.9% by weight relative to the total weight of the composition.

4. The composition of claim 3 wherein the water is present in an amount of from about 40% to about 80% by weight relative to the total weight of the composition.

5. The composition of claim 3 wherein the pH is from about 6.5 to about 7.5.

6. The composition of claim 1 wherein the at least one film former is a styrene/acrylates/ammonium methacrylate copolymer.

7. The composition of claim 1 wherein the acid is citric acid.

8. The composition of claim 7 that includes a pigment.

9. The composition of claim 8 wherein the viscosity is from about 70 Pa·s to about 350 Pa·s at 1/s.

10. The composition of claim 9 wherein the film former is present in an amount of from about 20% to about 37.5%, by weight relative to the total weight of the composition.

11. A cosmetic composition comprising:
(a) from about 20% to about 40%, by weight, of at least one latex film forming polymer, wherein the latex film forming polymer is an acrylate copolymer having a glass transition temperature from about −15° C. to about 90° C.;
(b) from about 0.5% to about 0.9%, by weight, of at least one acid having a pH of from about 1.0 to about 2.4 at Normality of 0.1 N;
(c) from about 40% to about 60% by weight, water; and
(d) at least one pigment;
wherein said composition has a viscosity from about 70 Pa·s to about 350 Pa·s, at a shear rate of 1/s, and a pH of from about 6.5 to about 8,
wherein all weights are relative to the total weight of the composition,
wherein the acrylate copolymer is selected from the group consisting of styrene/acrylates/ammonium methacrylate copolymers, styrene/acrylates copolymers emulsion, styrene acrylic copolymers, and mixtures thereof, and
wherein the acid is selected from the group consisting of citric acid, isocitric acid, formic acid, hydrochloric acid, lactic acid, malic acid, oxalic acid, tartaric acid, trichloroacetic acid, and mixtures thereof.

12. A method of improving the long-wear property of a mascara comprising including in said mascara the composition of claim 11.

13. A method of improving long-wear in a mascara composition comprising including in said composition (a) from about 20% to about 40%, by weight of at least one styrene/acrylate copolymer, (b) at least one acid having a pH of from about 1.0 to about 2.4 at Normality of 0.1 N; and (c) water,
wherein the styrene/acrylate copolymer has a glass transition temperature from about −15° C. to about 90° C., and
wherein the acid is selected from the group consisting of citric acid, isocitric acid, formic acid, hydrochloric acid, lactic acid, malic acid, oxalic acid, tartaric acid, trichloroacetic acid, and mixtures thereof.

* * * * *